(12) United States Patent
Weigl et al.

(10) Patent No.: US 8,318,936 B2
(45) Date of Patent: Nov. 27, 2012

(54) METHOD FOR PRODUCING N-METHYLNALTREXONE BROMIDE

(75) Inventors: Ulrich Weigl, Hilzingen (DE); Pascal Schär, Bern (CH); Alfred Stutz, Zürich (CH)

(73) Assignee: Cilag AG, Schaffhausen (CH)

( * ) Notice: Subject to any disclaimer, the term of this patent is extended or adjusted under 35 U.S.C. 154(b) by 347 days.

(21) Appl. No.: 12/600,341

(22) PCT Filed: May 14, 2008

(86) PCT No.: PCT/EP2008/003870
§ 371 (c)(1),
(2), (4) Date: Mar. 2, 2010

(87) PCT Pub. No.: WO2008/138605
PCT Pub. Date: Nov. 20, 2008

(65) Prior Publication Data
US 2010/0168427 A1     Jul. 1, 2010

(30) Foreign Application Priority Data
May 16, 2007   (WO) ................. PCT/EP2007/004365

(51) Int. Cl.
*C07D 489/08* (2006.01)
*C07D 489/02* (2006.01)
(52) U.S. Cl. .......................................... 546/45; 546/44
(58) Field of Classification Search .................. 514/282; 546/45, 44
See application file for complete search history.

(56) References Cited

U.S. PATENT DOCUMENTS
7,645,880 B2 * 1/2010 Dlubala .......................... 546/45

FOREIGN PATENT DOCUMENTS
| WO | WO 2004/043964 A2 | 5/2004 |
| WO | WO 2006/127899 A2 | 11/2006 |
| WO | WO 2008/034973 A1 | 3/2008 |

* cited by examiner

*Primary Examiner* — Charanjit Aulakh
(74) *Attorney, Agent, or Firm* — Hoffmann & Baron, LLP

(57) ABSTRACT

Process for the preparation of N-methylnaltrexone bromide, wherein a compound of the general formula (I):

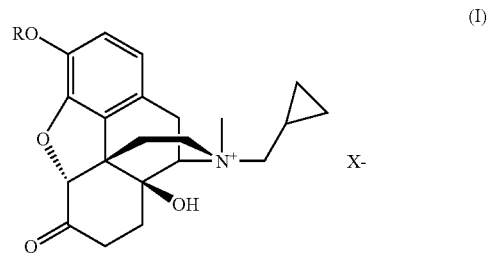

wherein
$X^-$ represents an anion other than the bromide anion, and R represents hydrogen or a leaving group, is dissolved or dispersed in a suitable polar solvent, the solution or dispersion is mixed with a compound containing bromide anions, and the resulting reaction mixture is stirred until N-methylnaltrexone bromide has formed and crystallized, wherein, in the case where R represents a leaving group, that group is removed during or after the reaction.

18 Claims, No Drawings

METHOD FOR PRODUCING N-METHYLNALTREXONE BROMIDE

CROSS-REFERENCE RELATED APPLICATIONS:

This application is the National Stage of International Application No. PCT/EP2008/003870, filed May. 14, 2008, which claims the benefit of International Application No. PCT/EP2007/004365, filed May. 16, 2007, the entire contents of both of which are incorporated by reference herein.

FIELD OF THE INVENTION:

The present invention relates to a process for the preparation of N-methylnaltrexone bromide.

BACKGROUND OF THE INVENTION:

N-Methylnaltrexone bromide (CAS No. 73232-52-7) is a known pharmaceutically active compound which is used in particular for the treatment of post-operative ileus or for the treatment of opioid-induced constipation. N-Methyl-naltrexone bromide is also referred to as naltrexone methobromide and corresponds to the chemical formula:

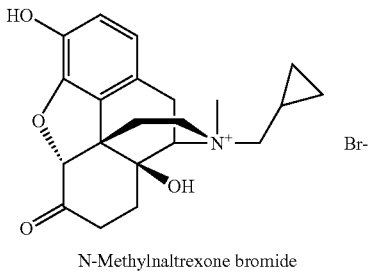

N-Methylnaltrexone bromide

The compound N-methylnaltrexone bromide is described in U.S. Pat. No. 4,176,186. The compound is prepared, for example, by reacting the free naltrexone base with methyl bromide. This process has the disadvantage that the reaction must be carried out in a pressurised vessel in an organic solvent, such as anhydrous acetone and/or dimethylformamide, for a comparatively long period of time. In addition, undesirable secondary products are formed in the reaction. In U.S. Pat. No. 4,176,186 it is also proposed to methylate the free naltrexone base with methyl iodide or dimethyl sulfate in a first step and then exchange the anion present in the resulting compound for the bromide anion by means of chromatography. A bromide-loaded chromatographic ion exchanger is used thereby. Chromatographic ion exchange is not suitable for the preparation of methylnaltrexone bromide in relatively large amounts, however, because it is very intensive in terms of time, volume and solvent and is therefore too expensive for industrial use. There is therefore a need for a process for the preparation of methylnaltrexone bromide that can be carried out simply and inexpensively on an industrial scale.

SUMMARY OF THE INVENTION:

It has now been found that it is possible, surprisingly, to methylate the free naltrexone base on the nitrogen atom with a suitable bromide-free methylating agent in a manner known per se and then exchange the anion present in the methylated quaternary compound for the desired bromide anion in a simple manner and without using chromatographic ion exchange technology. The exchange of the anions is thereby carried out in a solution or suspension of the resulting quaternary compound in a suitable polar solvent, such as, for example, water, alcohol or a mixture of those compounds, by simply adding a compound containing bromide anions, which compound is preferably likewise dissolved in a polar solvent. The methylnaltrexone bromide so formed is precipitated in the form of a crude product, optionally after prior cleavage of the protecting group on the phenolic group, in a purity of at least 99% (purity >99%). After subsequent recrystallisation, for example from water/methanol, the value of the bromide content corresponds with the theoretically calculated amount of bromide anions in the methylnaltrexone bromide to the extent of at least 99.99% (>99.99%). This process is suitable for the inexpensive preparation of large amounts of methylnaltrexone bromide because it involves only simple crystallisation processes and not expensive ion chromatography.

The process according to the invention is based in particular on the different solubility of the methyl-naltrexone salt, for example methylnaltrexone methyl sulfate, that is present after the alkylation, as compared with methylnaltrexone bromide. Because methylnaltrexone bromide is markedly less soluble in the solvents used than is the methylnaltrexone methyl sulfate mentioned by way of example, the exchange of anions takes place virtually quantitatively.

DETAILED DESCRIPTION:

The present invention is defined in the claims. In particular, the present invention relates to a process for the preparation of N-methylnaltrexone bromide which is characterised in that a compound of the general formula (I):

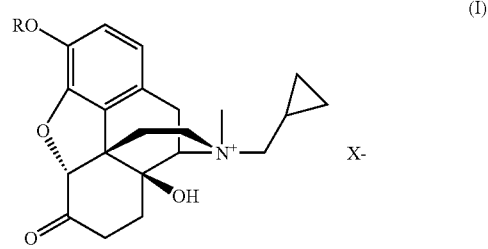

wherein
X⁻ represents an anion other than the bromide anion, and
R represents hydrogen or a leaving group,
(i) is dissolved or dispersed in a suitable polar solvent,
(ii) the solution or dispersion is mixed with a compound containing bromide anions, and the resulting reaction mixture is stirred until N-methylnaltrexone bromide has formed and crystallised, wherein, in the case where R represents a leaving group, that group is removed during or after the reaction.

X⁻ preferably represents Cl⁻; I⁻; HSO$_4^-$; SO$_4^{2-}$; [—O—S(O)$_2$—O—(C$_{1-4}$)alkyl], preferably [—O—S(O)$_2$—O—CH$_3$]; [—O—S(O)$_2$—(C$_{1-4}$)alkyl], preferably [—O—S(O)$_2$—CH$_3$]; [—O—S(O)$_2$—CF$_3$]; [—O—S(O)$_2$-phenyl], wherein the phenyl ring is optionally substituted, preferably in the para-position, preferably by methyl.

X⁻ preferably represents HSO$_4^-$; SO$_4^{2-}$; [—O—S(O)$_2$—O—CH$_3$]; [—O—S(O)$_2$—(C$_{1-4}$)alkyl]; [—O—S(O)$_2$—CF$_3$]; [—O—S(O)$_2$-phenyl]; or [—O—S(O)$_2$-tolyl]. Preferably, $X^-$ represents: $HSO_4^-$, $SO_4^{2-}$, [—O—S(O)$_2$—O—CH$_3$], [—O—S(O)$_2$—CH$_3$], [—O—S(O)$_2$-phenyl] or [—O—S(O)$_2$-tolyl].

$X^-$ preferably represents: $HSO_4^-$; $SO_4^{2-}$; [—O—S(O)$_2$—O—CH$_3$]; [—O—S(O)$_2$—CH$_3$]; [—O—S(O)$_2$-phenyl]; and preferably $HSO_4$ $SO_4^{2-}$, [—O—S(O)$_2$—O—CH$_3$] or [—O—S(O)$_2$—CH$_3$]

R preferably represents hydrogen or a leaving group, preferably hydrogen. The presence of the protecting group R, or cleavable protecting group R, is not necessary in order to carry out the exchange of anions according to the invention. However, the use of a compound of the general formula (I) wherein R represents a leaving group is expedient when that leaving group is present as a result of the preceding methylation reaction. The protecting group can then also be removed after the anion exchange reaction, the reaction conditions for the removal of the leaving group being known per se and varying depending on the protecting group. The reaction according to the invention for exchanging the anions can also be carried out under conditions such that the leaving group is cleaved during the exchange reaction. This is possible when the leaving group can be cleaved under the conditions of the ion exchange, for example with aqueous HBr.

There is used as the leaving group R preferably ($C_1$-$C_8$)-alkyloxycarbonyl or phenyloxycarbonyl; preferably ethyloxy-carbonyl, isobutyloxycarbonyl, or tert-butyloxycarbonyl (Boc), cyclohexyloxycarbonyl, or trialkylsilyl; preferably ($C_1$-$C_8$)-alkyloxycarbonyl or phenyloxycarbonyl; preferably ethyloxycarbonyl or tert-butyloxycarbonyl (Boc) or trialkylsilyl, such as, for example, trimethylsilyl, starting, for example, from (CH$_3$)$_3$SiCl or hexamethyl-disilazane and other organosilyl compounds known per se. Preferably R represents: ($C_1$-$C_8$)-alkyloxycarbonyl or phenyl-oxycarbonyl; preferably ethyloxycarbonyl or tert-butyloxy-carbonyl (Boc).

In addition to the mentioned protecting groups, ester groupings, such as, for example, methyl ester, acetyl ester, benzyl ester or optionally substituted benzyl ester groups, can also be used as the leaving group R.

For the introduction of an alkyloxycarbonyl group, for example ethyloxycarbonyl, there is used in a manner known per se ethyl chloroformate. The processes for the introduction of different protecting groups or cleavable leaving groups are known per se from the literature.

The compound of formula (I) is obtained by methylation of the free naltrexone base, which at the same time leads to the introduction of the anion $X^-$ and yields a compound of the general formula (I). Within that context, the present invention relates to a process for the preparation of the compound of formula (I), which process is characterised in that the free naltrexone base is reacted with a compound containing the substituent X, the phenolic hydroxyl group optionally being provided beforehand with a protecting group.

Examples of such compounds containing the substituent $X^-$ are: methyl chloride (CH$_3$Cl); methyl iodide (CH$_3$I); dimethyl sulfate [CH$_3$—O—S(O)$_2$—O—CH$_3$]; (C$_{1-4}$)alkylsulfonic acid methyl ester [CH$_3$—O—S(O)$_2$—(C$_{1-4}$)alkyl]; preferably methylsulfonic acid methyl ester [CH$_3$—O—S(O)$_2$ —CH$_3$]; trifluoromethylsulfonic acid methyl ester [CH$_3$—O—S(O)$_2$—CF$_3$]; phenylsulfonic acid methyl ester [CH$_3$—O—S(O)$_2$-phenyl], wherein the phenyl ring is optionally substituted, preferably in the para-position, preferably by methyl. There are preferably used for the methylation the mentioned sulfate compounds and sulfonate compounds, so that the substituents $X^-$ as also defined herein in the preferred embodiments are obtained.

The methylation of the free naltrexone base, which yields the compound of the general formula (I), is preferably carried out under substantially anhydrous conditions. Preference is given, also as solvents, to those compounds which simultaneously contain the methyl group for the methylation of the free naltrexone base and also the required anion ($X^-$), which yields the compound of the general formula (I). These preferred compounds correspond to the compounds already mentioned hereinbefore: methyl chloride, methyl iodide, dimethyl sulfate, (C$_{1-4}$)alkyl-sulfonic acid methyl ester, such as methylsulfonic acid methyl ester, trifluoromethylsulfonic acid methyl ester, phenylsulfonic acid methyl ester, wherein the phenyl ring is optionally substituted, preferably in the para-position, preferably by methyl. Preferred compounds for the methylation are in particular the mentioned sulfate compounds and sulfonate compounds, which yield the substituents $X^-$ as defined herein in the preferred embodiments.

The resulting compound of formula (I), for example the methyl carbonate methyl sulfate, is preferably isolated by a precipitation reaction, for example by the addition of ethyl acetate or another compound that is miscible with the alkylating agent, for example dimethyl sulfate. Examples of such other compounds are ethyl acetate, methyl acetate, tert-butyl methyl ether, toluene, tetrahydrofuran and 2-methyltetrahydrofuran. Solvents of similar polarity can readily be added to this list by the person skilled in the art.

According to the invention, the compound of formula (I) is dissolved or dispersed in a suitable polar solvent [step (i)], that polar solvent containing the compound of formula (I) being mixed with a compound containing bromide anions. The resulting reaction mixture is thereby stirred until the N-methylnaltrexone bromide has formed and crystallised. Accordingly, methylnaltrexone bromide is obtained by addition of hydrogen bromide or by addition of bromides, for example sodium bromide, potassium bromide, ammonium bromide, dissolved in suitable polar protic solvents. Suitable polar solvents for obtaining and precipitating methylnaltrexone bromide are, for example, water as well as polar organic solvents, such as aprotic dipolar solvents such as dimethylacetamide (DMA), dimethyl-formamide (DMF), N-methylpyrrolidone (NMP) or dimethyl sulfoxide (DMSO), alcohols, preferably aliphatic alcohols. Preference is given to the systems water, water/methanol, water/ethanol, dimethylformamide, dimethylacetamide, N-methylpyrrolidone, acetonitrile, acetone/dimethylformamide and acetone/dimethylacetamide, in particular aliphatic (C$_{1-4}$)-alcohols or a mixture of such polar organic solvents with water.

According to the invention, strongly acidic conditions are employed for the precipitation reaction, such conditions also being obtained, for example, by the aqueous decomposition of the alkylating agent, for example of dimethyl sulfate, to sulfuric acid. Water is generally present, as an excess for destroying the alkylating agent, in small amounts.

Preferred alcohols are (C$_{1-4}$)-alcohols, preferably methanol, ethanol, propanol, butanol, preferably methanol. The compound of formula (I) is thereby dissolved or dispersed in the mentioned polar solvents, preferably at room temperature, preferably at a temperature in the range from 20° C. to 80° C., preferably from 20° C. to 70° C., preferably from 20° C. to 65° C., preferably with stirring, the compound containing the bromide anion being added and stirring being carried out, preferably at elevated temperature, until the desired N-methylnaltrexone bromide has formed in a quantitative amount. The reaction generally requires a time of from only a few minutes, for example approximately 5 minutes, to approximately 20 hours, stirring preferably being carried out for from 4 to 8 hours. For the quantitative isolation of the bromide that has formed, the reaction mixture is preferably cooled at least to room temperature, preferably to a temperature in the range from room temperature (about 20° C.) to −30° C. The concentration of the compound of formula (I) in the solvent is thereby so chosen that the resulting N-methylnaltrexone bromide precipitates in a quantitative amount, while the remaining components remain dissolved. This is a process optimisation for specifying in each case the optimum concentration of the compound of formula (I) in the solvent in question and presents no problems to the person skilled in the art.

The compound containing at least one bromide anion can be added as such to the solution or dispersion of the compound of formula (I). The compound containing at least one bromide anion is preferably dissolved in water or a polar organic solvent, the polar organic solvent being selected from the group comprising: water, polar organic solvents, aprotic dipolar solvents, preferably dimethylacetamide (DMA), dimethylformamide (DMF), N-methylpyrrolidone (NMP) or dimethyl sulfoxide (DMSO); alcohols, preferably aliphatic alcohols, preferably aliphatic ($C_{1-4}$)-alcohols or a mixture of such polar organic solvents with water; preferably water or a mixture of water and alcohol with any desired water content. The presence of water is not necessary for the ion exchange and the concentration of any water that may be present is not critical.

There are a large number of suitable compounds containing bromide anions, and they can be inorganic or organic compounds. Of course, only medically approved compounds are used. Accordingly, it is possible to use, for example, heavy metal bromides, organic bromides, bromide-cleaving phosphonium salts, and many other compounds. Preference is given to hydrobromic acid (HBr); alkali bromides, such as sodium bromide or potassium bromide; alkaline earth bromides, such as calcium bromide; quaternary, inorganic or organic ammonium bromides, such as ammonium bromide ($NH_4Br$) or dimethylammonium bromide. Sodium bromide and dimethyl-ammonium bromide are preferred.

The anion exchange reaction according to the invention is preferably carried out at an acid value (pH value) in the range from zero to 9 (nine), preferably in the range from zero to 5 (five), preferably in the range from zero to 3 (three), that acid value preferably being established by adding hydrobromic acid (HBr) to the reaction mixture.

According to the invention, the methylation reaction and the exchange of the anion obtained by the methylation for the bromide anion can be carried out directly after one another. Within that context, the present invention relates to a process for the preparation of N-methylnaltrexone bromide, which process is characterised in that a compound of formula (I) is prepared in a first step by reacting the free naltrexone base with a compound containing the substituent X, the phenolic hydroxyl group of the free naltrexone base optionally being provided beforehand with a protecting group, and then, in a second step, the resulting compound of the general formula (I) is dissolved or dispersed in a suitable polar solvent, the solution or dispersion is mixed with a compound containing bromide anions, and the reaction mixture, or the solution or dispersion, is stirred until N-methylnaltrexone bromide has formed and crystallised, wherein, in the case where R represents a leaving group, that group is removed during or after the reaction. The conditions for carrying out the individual steps correspond to the conditions mentioned hereinbefore.

According to a particular embodiment of the present invention, it is also possible to carry out both the methylation and the exchange of the anion obtained by the methylation for the bromide anion directly after one another without isolating the compound of formula (I) from the reaction mixture (one-pot process). If a methyl sulfate, such as, for example, dimethyl sulfate, or an alkylsulfonic acid methyl ester, such as, for example, methylsulfonic acid methyl ester or trifluoromethylsulfonic acid methyl ester or a phenylsulfonic acid methyl ester, is used as the methylating agent for the preparation of the compound of formula (I), it is necessary in the one-pot process to decompose the excess toxic methylating agent in situ and to remove a protecting group that may be present bonded to the phenolic group. It has been found that both are possible, surprisingly, in the presence of water without damaging the resulting sulfate or sulfonate of the compound of formula (I). The process has the advantage that the decomposition of the excess toxic methylating agent can be carried out at a neutral or acid pH value (pH$\leqq$7), preferably at an acid pH value, the acidic decomposition products of the methyl sulfate compound, for example of dimethyl sulfate, or of the sulfonic acid methyl ester compound effecting a comparatively constant acid pH value during the reaction. In the decomposition of dimethyl sulfate, for example, sulfuric acid is also formed, which then gives for the meaning of $X^-$ in the compound of formula (I) $HSO_4^-$ ($X^-=HSO_4^-$) or $SO_4^{2-}$ ($X=SO_4^2$).

It is also possible, however, to carry out the decomposition of the excess toxic methylating agent in the one-pot process at an elevated acid value (pH 8-12), a base, such as, for example, sodium hydroxide solution or aqueous ammonia, being added to the reaction mixture in order to achieve the basic pH value. However, this embodiment has the disadvantage that a further reagent must be metered in during the process. Also, the crystallisation of the methylnaltrexone bromide after addition of the bromide source is preferably carried out in an acidic medium.

Harmless secondary products form from the excess toxic methylating agent both at an acid and at a basic pH value. In the reaction mixture, containing the compound of formula (I) and the non-toxic secondary products, the compound of formula (I) can be converted into methylnaltrexone bromide by addition of a bromide source, for example of aqueous hydrogen bromide (HBr). The methylnaltrexone bromide crystallises out in pure form as the crude product and can optionally be recrystallised, an acid pH value preferably being used for the crystallisation.

The one-pot process is particularly suitable for the inexpensive preparation of large amounts of methyl-naltrexone bromide, because the isolation of the methyl-naltrexone bromide does not require any special safety precautions since, according to this embodiment, the vapour pressure of the methylating agent in the reaction solution, for example of the remaining toxic dimethyl sulfate, is less than 0.1 ppm (<0.1 ppm), measured in the vapour phase of the solution at 70° C.

Within that context, the present invention relates to a one-pot process for the preparation of N-methylnaltrexone bromide, which process is characterised in that a compound of the general formula (I) is prepared by reacting the free naltrexone base with a methylating agent containing the substituent X, as is described hereinbefore, the phenolic hydroxyl group of the free naltrexone base optionally being provided beforehand with a protecting group, and then, in the case where the compound of the general formula (I) is a sulfate or sulfonate, the excess methylating reagent present in the reaction mixture is decomposed in the presence of water, preferably at a neutral or acid pH value (pH 7), preferably at an acid pH value, and at elevated temperature, so that a protecting group that may be present, bonded to the phenolic group, is removed at the same time; and then a compound containing bromide anions is added to the reaction mixture and stirring is carried out until N-methylnaltrexone bromide has formed and crystallised.

The present invention relates also to the one-pot process defined hereinbefore for the preparation of N-methyl-naltrexone bromide, which process is characterised in that the decomposition of the excess methylating agent present in the reaction mixture is carried out at an elevated acid value (pH 8-12), a base, such as, for example, sodium hydroxide solution or aqueous ammonia, being added to the reaction mixture in order to achieve the basic pH value. Crystallisation of the N-methylnaltrexone bromide is then preferably carried out in an acidic medium.

For the decomposition of the excess methylating agent present in the reaction mixture there is preferably used at least one equivalent of water, based on the excess alkylating agent. It is preferred to use an excess of water, for example from 1.1 to 5.0 equivalents of water or of another reagent that destroys the alkylating agent, based on the excess alkylating agent still present, and the reaction mixture is preferably heated for from 4 to 8 hours at a temperature in the range from 50° C. to 90° C., preferably from 70° C. to 80° C. Under those conditions, the excess alkylating agent is destroyed and any leaving groups present are removed.

According to the invention, the procedure followed in the one-pot process is preferably as follows: naltrexone alkyl ethyl carbonate, for example, is methylated, for example with dimethyl sulfate, preferably for a period of approximately from 10 to 20 hours, at a temperature of preferably from 50° C. to 60° C. The excess dimethyl sulfate is then decomposed by adding water to the reaction mixture and heating at approximately from 70° C. to 80° C. for approximately from 4 to 8 hours, until the measured value in the vapour pressure of the solution is less than 0.1 ppm. Methanol and aqueous HBr solution are then added to the reaction mixture, whereupon methylnaltrexone bromide forms and crystallises out.

The N-methylnaltrexone bromide crude product so obtained is in each case preferably recrystallised from a suitable solvent, preferably from water or aqueous alcohol, preferably from aqueous alcohol, preferably from ethanol or methanol, preferably from methanol, containing from 1% to 99% water, based on the total weight of water and methanol. In the case of recrystallisation from water/methanol or water, a value of the bromide content that corresponds to the extent of at least 99.99% (>99.99%) with the theoretically calculated amount of bromide ions in the methylnaltrexone bromide is achieved. Preference is given to crystallisation from a saturated solution, as is known to the person skilled in the art.

The present invention relates also to the use of the N-methylnaltrexone bromide prepared according to the invention as a medicament and to the use of the N-methyl-naltrexone bromide prepared according to the invention in the preparation of a pharmaceutically administrable medicament, in particular for the treatment of post-operative ileus or for the treatment of opioid-induced constipation. The examples which follow explain the invention without limiting it.

EXAMPLE 1

(A) 30 g of naltrexone ethyl carbonate [containing ethyloxycarbonyl as leaving group on the phenolic hydroxyl group] are dissolved in 60 g of dimethyl sulfate and stirred for 16 hours (h) at 60° C. 30 g of ethyl acetate are then added. The resulting product is filtered off with suction, washed with ethyl acetate and dried in vacuo. 36 g of methylnaltrexone ethyl carbonate methyl sulfate having a purity of 96% are isolated.

(B) 30 g of methylnaltrexone ethyl carbonate methyl sulfate, obtained according to section (A), are suspended in methanol; aqueous dimethylamine solution is added, and stirring is carried out for one hour at room temperature. The acid value (pH value) is then adjusted to below 5 (pH <5) using aqueous HBr solution, whereupon the leaving group is cleaved and the methylnaltrexone bromide crystallises out as the crude product. 22 g of crude methylnaltrexone bromide having a purity of greater than 99% (purity >99%) are obtained.

(C) 20 g of methylnaltrexone bromide crude product, obtained according to section (B), are dissolved at boiling heat (at 65° C.) in a mixture of water/methanol/HBr, consisting of water:methanol:HBr of 20 g:40 g:0.5 mol % and crystallised out by cooling to 0° C. 17 g of methylnaltrexone bromide having a purity of at least 99.8% (purity >99.8%) and a bromide content of 18.3% are obtained. The amount of methyl sulfate is less than 0.01 wt. %.

EXAMPLE 2

20 g of naltrexone ethyl carbonate are dissolved in 30 g of dimethyl sulfate and stirred for 10-20 hours at 50-60° C. 25 g of water are then added and stirring is carried out for approximately 5 hours at 70-80° C. 60 g of methanol are then added, and 25 g of an aqueous HBr solution (48 wt. %) are added dropwise at 50° C. The resulting product is filtered off with suction at reduced temperature and then washed with methanol and dried in vacuo. 19.2 g of methyl-naltrexone bromide (as the crude product) are obtained.

EXAMPLE 3

16.59 g of methylnaltrexone bromide (as the crude product), prepared according to Example 2, are dissolved at boiling heat in 19.89 g of water and 0.7 g of NaBr and crystallised out by cooling to 0° C. 14.59 g of methylnaltrexone bromide having a purity of >99.8% and a bromide content of 18.3% are obtained. The amount of dimethyl sulfate is <5 ppm.

EXAMPLE 4

Preparation of Naltrexone/Introduction of Protecting Group a) 100 g of noroxymorphone are suspended in 165 g of N-methylpyrrolidinone and 37 g of sodium carbonate, and 56 g of bromomethylcyclopropane are added. The suspension is heated for 3 hours at 70° C. Cooling is then carried out, and the product is crystallised by means of 803 g of water.

Inoculation with naltrexone is thereby carried out. At the end of the addition of water, the pH value is adjusted to 9.5 by addition of sodium hydroxide solution. The product is filtered off with suction, washed with water and dried in vacuo.

Yield: 113 g of crude naltrexone, purity >95%.

b) 50 g of crude naltrexone and 1.7 g of activated carbon are heated for one hour at reflux in 400 g of ethyl acetate. The activated carbon is then filtered off. Half the amount of ethyl acetate is distilled off. 21 g of triethylamine and 18 g of chloroformic acid ethyl ester are added, and the mixture is heated for one hour at 45° C.; 100 g of water are then added and the phases are separated. The organic phase is washed again with 100 g of water and then concentrated to a minimum at normal pressure. In order to complete the crystallisation, 218 g of isopropanol are added. The suspension is cooled to 0° C. The product is filtered off with suction, washed with isopropanol and dried in vacuo.

Yield: 53 g of naltrexone carbonate, purity >99.3%.

EXAMPLE 5

Precipitation of Intermediate with Tert-Butyl Methyl Ether 30 g of naltrexone ethyl carbonate are dissolved in 60 g of dimethyl sulfate and stirred for 16 hours at 60° C. 20 g of tert-butyl methyl ether are then added. The resulting product is filtered off with suction and then washed with tert-butyl methyl ether and dried in vacuo. 36.5 g of methylnaltrexone carbonate methyl sulfate having a purity of >95% are isolated.

EXAMPLE 6

Precipitation of the Intermediate with Toluene 30 g of naltrexone ethyl carbonate are dissolved in 50 g of dimethyl sulfate and stirred for 20 h at 60° C. 20 g of toluene are then added. The resulting product is filtered off with suction and then washed with toluene and dried in vacuo. 34 g of methylnaltrexone ethyl carbonate methyl sulfate having a purity of >95% are isolated.

EXAMPLE 7

Methylation with Trifluoromethylsulfonate 30 g of naltrexone ethyl carbonate are dissolved in 50 g of trifluoromethylsulfonic acid methyl ester and stirred for 8 hours at 40° C. 30 g of ethyl acetate are then added. The resulting product is filtered off with suction and then washed with ethyl acetate and dried in vacuo. 37.8 g of methylnaltrexone ethyl carbonate trifluoromethylsulfonate having a purity of >96% are isolated.

EXAMPLE 8

Methylation with p-toluenesulfonic acid methyl ester 30 g of naltrexone ethyl carbonate are dissolved in 50 g of dimethylacetamide and stirred for 48 hours at 60° C. with 30 g of p-toluenesulfonic acid methyl ester. 40 g of ethyl acetate are then added. The resulting product is filtered off with suction and then washed with ethyl acetate and dried in vacuo. 33.2 g of methylnaltrexone ethyl carbonate p-toluenesulfonate having a purity of >96% are isolated.

EXAMPLE 9

Precipitation of the Crude Product from Methanol/HBr 30 g of methylnaltrexone ethyl carbonate methyl sulfate are suspended in methanol; gaseous dimethylamine is added, and stirring is carried out for one hour at room temperature. The mixture is then acidified (pH value <5) by addition of a solution of HBr in methanol (approx. 10% strength), whereupon methylnaltrexone bromide crystallises out. The product is filtered off with suction, washed with methanol and dried in vacuo. 22.5 g of crude methylnaltrexone bromide having a purity of >99% are obtained.

EXAMPLE 10

Precipitation of the Crude Product from Ethanol/HBr 30 g of methylnaltrexone ethyl carbonate methyl sulfate are suspended in ethanol; aqueous dimethylamine solution is added and stirring is carried out for one hour at room temperature. The pH value is then adjusted to <5 by addition of a solution of HBr in ethanol (approx. 5% strength), whereupon methylnaltrexone bromide crystallises out. The product is filtered off with suction, washed with ethanol and dried in vacuo. 21 g of crude methylnaltrexone bromide having a purity of >98% are obtained.

What is claimed is:

1. Process for the preparation of N-methylnaltrexone bromide, wherein a compound of the general formula (I):

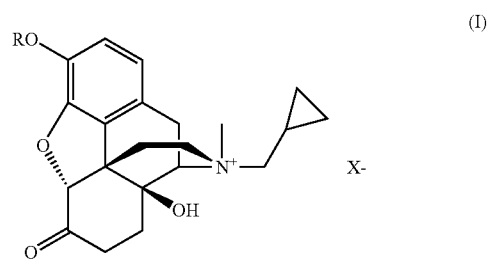

wherein
X$^-$ represents an anion selected from HSO$_4^-$; SO$_4^{2-}$; [—O—S(O)$_2$—O—(C$_{1-4}$)alkyl]; [—O—S(O)$_2$—(C$_{1-4}$)alkyl];
[—O—S(O)$_2$—CF$_3$]; or [—O—S(O)$_2$-phenyl], wherein the phenyl ring is optionally substituted;
R represents hydrogen or a leaving group,
(i) is dissolved or dispersed in a suitable polar solvent, said solvent being selected from the group consisting of water, polar organic solvents, aprotic dipolar solvents, and alcohols or a mixture thereof;
(ii) the solution or dispersion is mixed with a compound containing bromide anions, and the resulting reaction mixture is stirred until N-methylnaltrexone bromide has formed and crystallised, wherein, in the case where R represents a leaving group, that group is removed during or after the reaction.

2. Process according to claim 1, wherein X$^-$ represents: HSO$_4^-$; SO$_4^{2-}$; [—O—S(O)$_2$—O—CH$_3$]; [—O—S(O)$_2$—CH$_3$]; [—O—S(O)$_2$-phenyl]; or [—O—S(O)$_2$-tolyl].

3. Process according to claim 1, wherein X$^-$ represents: HSO$_4^-$; SO$_4^{2-}$; [—O—S(O)$_2$—O—CH$_3$]; [—O—S(O)$_2$—CH$_3$]; or [—O—S(O)$_2$-phenyl].

4. Process according to claim 1, wherein R represents hydrogen.

5. Process according to claim 1, wherein R represents a leaving group selected from the group consisting of (C$_1$-C$_8$)-alkyloxycarbonyl, phenyloxycarbonyl, and trialkylsilyl.

6. Process according to claim 1, wherein R represents a leaving group selected from the group comprising ester groupings.

7. Process according to claim 1, wherein the solvent is selected from the group consisting of water, water/methanol, water/ethanol, dimethylformamide, dimethylacetamide, N-methylpyrrolidone, dimethyl sulfoxide, acetonitrile, acetone/dimethylformamide, and acetone/dimethylacetamide, aliphatic alcohols and mixtures of such polar organic solvents with water.

8. Process according to claim 1, wherein the compound of formula (I) is reacted with a compound containing bromide anions.

9. Process according to claim 1, wherein the compound containing bromide anions is selected from the group consisting of inorganic and organic medically approved compounds.

10. Process according to claim 1, wherein the anion exchange reaction is carried out at an acid value (pH value) in the range from zero to 9 (nine), the acid value preferably being established by adding hydrogen bromide (HBr) to the reaction mixture.

11. Process for the preparation of N-methylnaltrexone bromide, wherein a compound of formula (I) according to claim 1 is prepared in a first step by reacting the free naltrexone base with a compound containing the substituent X, the phenolic hydroxyl group of the free naltrexone base optionally being provided beforehand with a leaving group, and then, in a second step, the resulting compound of the general formula (I) is dissolved or dispersed in a suitable polar solvent, the solution or dispersion is mixed with a compound containing bromide anions, and the reaction mixture, or the solution or dispersion, is stirred until N-methylnaltrexone bromide has formed and crystallised, wherein, in the case where R represents a leaving group, that group is removed during or after the reaction, wherein said leaving group is selected from the group consisting of ($C_1$-$C_8$-alkyloxycarbonyl, phenyloxycarbonyl, trialkylsilyl, and ester groupings;
  wherein said solvent is selected from the group consisting of water, water/methanol, water/ethanol, dimethylformamide, dimethylacetamide, N-methylpyrrolidone, dimethyl sulfoxide, acetonitrile, acetone/dimethylformamide, and acetone/dimethylacetamide, aliphatic alcohols and mixtures of such polar organic solvents with water; and
  wherein said compound containing bromide anions is selected from the group consisting of inorganic and organic medically approved compounds.

12. Process according to claim 11, wherein the compound containing the substituent X is selected from the group consisting of dimethyl sulfate [$CH_3$—O—$S(O)_2$—O—$CH_3$]; ($C_{1-4}$) alkylsulfonic acid methyl ester [$CH_3$—O—$S(O)_2$—($C_{1-4}$)alkyl]; trifluoromethylsulfonic acid methyl ester [$CH_3$—O—$S(O)_2$—$CF_3$];
  and phenylsulfonic acid methyl ester [$CH_3$—O—$S(O)_2$-phenyl], wherein the phenyl ring is optionally substituted.

13. Process according to claim 12, wherein the resulting compound of formula (I) is isolated by means of a precipitation reaction.

14. Process for the preparation of N-methylnaltrexone bromide as a one-pot process, wherein a compound of the general formula (I) according to claim 1 is prepared by reacting the free naltrexone base with a methylating agent containing the substituent X, the phenolic hydroxyl group of the free naltrexone base optionally being provided beforehand with a protecting group, and then, the excess methylating agent present in the reaction mixture is decomposed in the presence of water, at a neutral or acid pH value (pH$\leq$7) or at an acid pH value, and at elevated temperature, so that a protecting group that may be present, bonded to the phenolic group, is removed at the same time; and then a compound containing bromide anions is added to the reaction mixture and stirring is carried out until N-methyl-naltrexone bromide has formed and crystallised.

15. Process according to claim 14, wherein the decomposition of the excess methylating agent present in the reaction mixture is carried out at an elevated acid value (pH 8-12).

16. Process according to claim 1, wherein the resulting N-methylnaltrexone bromide crude product is recrystallised from a suitable solvent.

17. Process according to claim 10, wherein the anion exchange reaction is carried out at a temperature in the range of 20° C. to 80° C., until the N-methylnaltrexone bromide has formed in a quantitative amount.

18. Process according to claim 16, wherein the resulting N-methylnaltrexone bromide crude product is recrystallised from aqueous ethanol or methanol, containing from 1% to 99% water, based on the total weight of water and methanol.

* * * * *